United States Patent [19]

McGinnis

[11] Patent Number: 4,480,115

[45] Date of Patent: Oct. 30, 1984

[54] DIRECT HYDROGENATION OF CARBOXYLIC ACIDS TO ALCOHOLS AND ESTERS

[75] Inventor: James L. McGinnis, Middlesex, N.J.

[73] Assignee: Celanese Corporation, New York, N.Y.

[21] Appl. No.: 476,310

[22] Filed: Mar. 17, 1983

[51] Int. Cl.³ .................... C07C 67/00; C07C 29/136
[52] U.S. Cl. ................ 560/1; 260/410.9 R;
546/263; 560/85; 560/100; 560/106; 560/199;
560/229; 560/265; 568/814; 568/831; 568/885
[58] Field of Search .................. 560/1, 106, 265, 229,
560/100, 85, 199; 568/885, 814; 546/263;
260/410.9 R

[56] References Cited

U.S. PATENT DOCUMENTS

| | | | |
|---|---|---|---|
| 2,607,807 | 8/1952 | Ford | 568/885 |
| 2,965,660 | 12/1960 | Heise | 560/265 |
| 4,189,441 | 2/1980 | Braca | 568/885 |
| 4,260,820 | 4/1981 | Knifton | 560/265 |
| 4,268,689 | 5/1981 | Knifton | 560/265 |
| 4,270,015 | 5/1981 | Knifton | 560/265 |
| 4,355,173 | 10/1982 | Isogai | 560/265 |
| 4,398,039 | 8/1983 | Pesa | 560/265 |

OTHER PUBLICATIONS

Carnahan, J. Am. Chem. Soc., 77 pp. 3766–3768 (1955).

*Primary Examiner*—Michael L. Shippen
*Attorney, Agent, or Firm*—Depaoli & O'Brien

[57] ABSTRACT

This invention provides an improved process for direct hydrogenation of a carboxylic acid to its corresponding alcohol with synthesis gas in the presence of a homogeneous catalyst comprising a ruthenium compound and a Lewis Acid metal halide.

14 Claims, No Drawings

DIRECT HYDROGENATION OF CARBOXYLIC ACIDS TO ALCOHOL AND ESTERS

BACKGROUND OF THE INVENTION

The direct hydrogenation of carboxylic acids to the corresponding alcohols is a relatively difficult and inefficient reaction. One large scale method of producing alcohols from carboxylic acids is by an indirect method employing metallic sodium reduction of an ester derivative of the carboxylic acid corresponding to the desired alcohol product.

U.S. Pat. No. 1,839,974 describes a process for direct conversion of carboxylic acids to alcohols in the presence of a heterogeneous metal chromite catalyst at a relatively high temperature.

U.S. Pat. No. 2,607,807 describes a process for reduction of carboxylic acids to the corresponding alcohols with hydrogen in the presence of a solid phase ruthenium-containing hydrogenation catalyst.

A Journal of Organometallic Chemistry, 188, 109 (1980) publication describes homogeneous catalytic hydrogenation of free carboxylic acids in the presence of cluster ruthenium carbonyl hydrides. Acetic acid is reduced at 180° C. to ethyl acetate with a conversion of 18.7% in 48 hours. At 200° C., in 48 hours the conversion is 44.5% to ethyl acetate/ethanol (72/28).

Other prior art of interest with respect to the present invention are processes which employ heterogeneous or homogeneous ruthenium-containing catalysts in the presence of hydrogen and/or carbon monoxide to produce alcohols and esters, and the like, such as U.S. Pat. Nos. 3,285,948; 3,935,284; 4,189,441; 4,269,784; 4,323,513; and 4,339,545.

There is continuing research effort to develop improved catalysts and processes for conversion of carboxylic acids to the corresponding alcohols.

Accordingly, it is an object of this invention to provide an improved process for direct hydrogenation of a carboxylic acid to the corresponding alcohol product and/or the carboxylic acid ester of the corresponding alcohol product.

It is a further object of this invention to provide a homogeneous hydrogenation catalyst composition comprising soluble ruthenium compound and Lewis Acid metal halide components in a liquid phase medium.

Other objects and advantages of the present invention shall become apparent from the accompanying description and examples.

DESCRIPTION OF THE INVENTION

One or more objects of the present invention are accomplished by the provision of a process for direct hydrogenation of a carboxylic acid to the corresponding alcohol which comprises reacting a carboxylic acid with hydrogen and carbon monoxide in a liquid phase medium at a temperature between about 100°–350° C. and a pressure between about 200–10,000 psi in the presence of a soluble catalyst comprising a ruthenium compound and a Lewis Acid metal halide, to yield a product comprising an ester of the carboxylic acid and its corresponding alcohol:

$$RCO_2H \rightarrow RCO_2CH_2R + RCH_2OH$$

Benzoic acid is converted as follows:

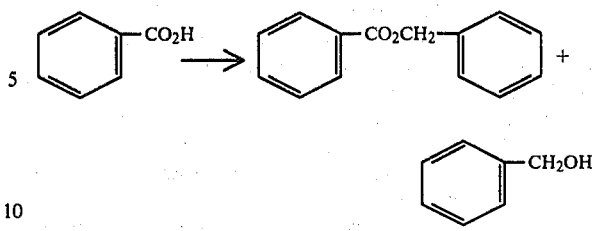

The carboxylic acid component can be essentially any free carboxylic acid compound that does not contain groups which interfere with the reactivity of the carboxylic group under the processing conditions.

Suitable carboxylic acids include $C_2$–$C_{30}$ aliphatic, alicyclic and aromatic compounds such as acetic acid, chloroacetic acid, caproic acid, caprylic acid, lauric acid, linoleic acid, crotonic acid, succinic acid, adipic acid, oxalic acid, cyclohexanecarboxylic acid, benzoic acid, fluorobenzoic acid, phthalic acid, terephthalic acid, naphthoic acid, nicotinic acid, and the like, and the corresponding salts such as sodium acetate and potassium benzoate.

The carboxylic acid component generally is employed in a quantity sufficient to function as a solvent medium. Optionally an inert diluent may be included as a solvent in the reaction medium. Illustrative of suitable solvents are hexane; octane; decalin; mineral oil; cyclohexane; benzene; tetrahydrofuran; diethyl ether; monoalkyl and dialkyl ethers of ethylene glycol, propylene glycol and diethylene glycol; methanol; butanol; 2-ethylhexanol; acetone; methyl ethyl ketone; methyl acetate; butyl acetate; methyl laurate; butyrolactone; water; perfluoroethane; monofluorobenzene; dimethylsulfone; sulfolane; and the like. The ester and/or alcohol products of the invention process can also be employed as a solvent to provide a homogeneous liquid phase reaction medium.

Under typical reaction conditions, the major product is the carboxylic acid ester of the corresponding alcohol which is formed by carboxylic acid reduction. The product mixture also contains the corresponding alcohol in the free form, and usually a small amount of the ether of the alcohol product. The proportion of the free alcohol component in the product mixture tends to increase as the quantity of water in the reaction medium increases.

An essential aspect of the invention process is the use of a homogeneous catalyst system comprising a ruthenium compound and a Lewis Acid metal halide as soluble components of the liquid phase reaction medium. Each of the co-catalyst components must be at least partially soluble in the liquid phase medium during the course of the process reaction.

Suitable ruthenium-containing compounds include ruthenium trichloride; ruthenium tribromide; ruthenium triiodide; tricarbonyl ruthenium(II) iodide; ruthenium nitrate; ruthenium acetate; ruthenium naphthenate; ruthenium valerate; ruthenium acetylacetonate; triruthenium dodecacarbonyl; tricarbonylruthenium(II) chloride dimer; and the like.

Illustrative of Lewis Acid metal halide compounds are chlorides, bromides, iodides and fluorides of metals such as aluminum, iron, zinc, gallium, cadmium, tin, antimony, and the like.

The term "metal halide" as employed herein is meant to include boron halides such as boron trifluoride. The term "Lewis Acid" refers to the G. N. Lewis concept of acid-base equilibria as elaborated in Chemical Reviews, 69(3), 251 (June 1969).

The ratio of ruthenium compound to the Lewis Acid metal halide in the catalyst composition can vary within a range between about 0.1–20:1, and preferably within a range between about 0.5–2:1.

The catalyst composition is employed in quantity between about 0.01–20 weight percent, based on the weight of carboxylic acid in the reaction medium, and preferably in the range between about 0.1–5 weight percent.

As demonstrated in Example V, without the presence of the Lewis acid metal halide co-catalyst component in the homogeneous reaction medium the process yields only a small quantity of desired carboxylic acid reduction products, and the main reaction is hydrogenation of carbon monoxide.

The hydrogen and carbon monoxide components of the reaction system are employed in a $H_2/CO$ molar ratio which can be varied in the range between about 1–30:30–1, with a typical $H_2/CO$ molar ratio being in the range of 1–5:5–1. Up to about 50 percent by volume of an inert gas as nitrogen or helium may be included in the $H_2/CO$ gasiform mixture.

The process is conducted at a temperature between about 100°–350° C., preferably between 200°–300° C.; and a pressure between about 200–10,000 psi, preferably between about 500–5000 psi; and for a reaction period between about 0.5–25 hours, as determined by the other parameters of the reaction system, such as temperature and pressure and the reactivity of the carboxylic acid compound.

The process can be conducted in a batch, semi-continuous or continuous manner. The catalyst may be initially introduced into the reaction zone batchwise, or it may be continuously or intermittently introduced during the course of the reaction. The reaction products may be recovered by distillation, fractionation, extraction, and the like. A fraction rich in the catalyst components may be recycled to the reaction zone, and additional products generated.

The following Examples are further illustrative of the present invention. The catalysts and other specific ingredients and processing parameters are presented as being typical, and various modifications can be derived in view of the foregoing disclosure within the scope of the invention.

EXAMPLES I–V

I $RuCl_3$ (25 mM in Ru) and $FeCl_3$ (84 mM) are stirred in acetic acid (100 ml) at 220° C. under 1:1 $H_2/CO$ at 3000–4600 psi in a reactor, and ethyl acetate is the major component of the product solution (46% by weight) after a 18.35 hour reaction period. Ethyl acetate+ethanol+diethyl ether represent 98% of the converted acetic acid. Conversion (excluding the acetate portion of the ester product) is about 39%. The conversion rates to $C_2H_5O$-derivatives are 13.1 moles/gm-atom Ru/hr and a STY of 0.33 mole/l/hr. Water gas shift activity is high, with $CO_2$ being formed at a rate of about 13.0 mole/gm-atom Ru/hr.

Benzoic acid converts to benzyl benzoate and cyclohexanecarboxylic acid converts to cyclohexylmethyl cyclohexanecarboxylate under similar conditions.

II

When propionic acid is the reactive solvent under similar conditions, the main products are propyl propionate and n-propanol. The conversion rates to $C_3H_7O$-derivatives are 7.8 mole/gm-atom Ru/hr and a STY of 0.20 mole/l/hr. The selectivity based on converted propionic acid is 94%.

III

A catalyst consisting of $RuCl_3$ (24 mM) and $SnCl_2$ (69 mM) in acetic acid at 190°–200° C. under 1:1 $H_2/CO$ at a total pressure of 4160–4220 psi in a reactor converts acetic acid to ethyl acetate with conversion rates of 4.2 moles/gm-atom Ru/hr and a STY of 0.10 mole/l/hr. The selectivity based on converted acetic acid is 99%.

IV

Under similar conditions as Example III, a $Ru_3(CO)_{12}$ (24 mM in Ru), $SnCl_2$ (112 mM) and $Fe(CO)_5$ (291 mM) catalyst in acetic acid provides a slower rate of hydrogenation. The acetic acid conversion rate is 0.26 mole/gm-atom Ru/hr, with about a 97% selectivity to ethyl acetate.

V

For purposes of comparison, $Ru_3(CO)_{12}$ (24 mM in Ru) in acetic acid without a Lewis Acid metal halide co-catalyst under the same general conditions (18.75 hr, 218°–219° C., 3800–4900 psi) yields mainly hydrogenation of CO, with a conversion rate to methyl acetate of 1.8 moles/gm-atom, Ru/hr, and a conversion rate to ethylene glycol diacetate of 0.053 mole/gm-atom Ru/hr. Ethyl acetate, either by reduction of the solvent or by homologation of methyl acetate, forms at a conversion rate of only 0.17 mole/gm-atom Ru/hr.

What is claimed is:

1. A process for direct hydrogenation of a carboxylic acid to the corresponding alcohol and formation of a corresponding ester which consists essentially of reacting a $C_2$–$C_{30}$ carboxylic acid with hydrogen and carbon monoxide in a liquid phase medium at a temperature between about 100°–350° C. and a pressure between about 200–10,000 psi in the presence of a soluble catalyst comprising a ruthenium compound and a Lewis Acid metal halide or boron halide to yield a product comprising an ester of the carboxylic acid and its corresponding alcohol.

2. A process in accordance with claim 1 wherein the carboxylic acid reactant is an aliphatic carboxylic acid.

3. A process in accordance with claim 1 wherein the carboxylic acid reactant is a cycloaliphatic carboxylic acid.

4. A process in accordance with claim 1 wherein the carboxylic acid reactant is an aromatic carboxylic acid.

5. A process in accordance with claim 1 wherein the carboxylic acid reactant is acetic acid, and the ester product comprises ethyl acetate.

6. A process in accordance with claim 1 wherein the carboxylic acid reactant is propionic acid, and the ester product comprises propyl propionate.

7. A process in accordance with claim 1 wherein the carboxylic acid reactant is cyclohexanecarboxylic acid, and the ester product comprises cyclohexylmethyl cyclohexanecarboxylate.

8. A process in accordance with claim 1 wherein the ruthenium compound is ruthenium halide.

9. A process in accordance with claim 1 wherein the ruthenium compound is ruthenium carbonyl.

10. A process in accordance with claim 1 wherein the Lewis Acid metal halide is metal chloride.

11. A process in accordance with claim 1 wherein the Lewis Acid metal halide is ferric chloride.

12. A process in accordance with claim 1 wherein the Lewis Acid metal halide is stannous chloride.

13. A process in accordance with claim 1 wherein the Lewis Acid metal halide is aluminum chloride.

14. A process in accordance with claim 1 wherein the Lewis Acid metal halide is boron trifluoride.

* * * * *